(12) United States Patent
Hiratsuka et al.

(10) Patent No.: US 8,987,204 B2
(45) Date of Patent: Mar. 24, 2015

(54) BONE REGENERATION AGENT COMPRISING GELATIN

(75) Inventors: Takahiro Hiratsuka, Ashigarakami-gun (JP); Shouji Ooya, Ashigarakami-gun (JP); Ichiro Nishimura, Santa Monica, CA (US)

(73) Assignee: FUJIFILM Coporation, Tokyo (JP)

( * ) Notice: Subject to any disclaimer, the term of this patent is extended or adjusted under 35 U.S.C. 154(b) by 0 days.

(21) Appl. No.: 13/394,263

(22) PCT Filed: Sep. 3, 2010

(86) PCT No.: PCT/JP2010/065108
§ 371 (c)(1),
(2), (4) Date: Mar. 5, 2012

(87) PCT Pub. No.: WO2011/027850
PCT Pub. Date: Mar. 10, 2011

(65) Prior Publication Data
US 2012/0165263 A1 Jun. 28, 2012

(30) Foreign Application Priority Data

Sep. 4, 2009 (JP) ................................. 2009-204218
Sep. 2, 2010 (JP) ................................. 2010-196678

(51) Int. Cl.

| | | |
|---|---|---|
| *A61K 38/16* | (2006.01) | |
| *A61K 38/17* | (2006.01) | |
| *A61K 38/39* | (2006.01) | |
| *A61P 19/08* | (2006.01) | |
| *A61P 19/10* | (2006.01) | |
| *A61K 9/14* | (2006.01) | |
| *A61K 9/16* | (2006.01) | |
| *C07K 14/78* | (2006.01) | |
| *C07K 14/51* | (2006.01) | |
| *A61K 38/00* | (2006.01) | |

(52) U.S. Cl.
CPC ................. *C07K 14/78* (2013.01); *C07K 14/51* (2013.01); *A61K 38/00* (2013.01)
USPC ....... 514/16.7; 514/16.8; 514/16.9; 514/21.2; 424/489; 424/492

(58) Field of Classification Search
None
See application file for complete search history.

(56) References Cited

U.S. PATENT DOCUMENTS

| | | |
|---|---|---|
| 6,992,172 B1 | 1/2006 | Chang et al. |
| 2009/0182063 A1 | 7/2009 | Bouwstra et al. |

FOREIGN PATENT DOCUMENTS

| | | |
|---|---|---|
| DE | 2756256 A1 | 6/1979 |
| JP | 2004-203829 A | 7/2004 |
| JP | 2007-528699 A | 10/2007 |
| WO | WO 2004/085473 A2 | 10/2004 |
| WO | 2007/040574 A2 | 4/2007 |
| WO | 2008103044 A1 | 8/2008 |
| WO | WO 2008/103041 A1 | 8/2008 |
| WO | WO 2008/103042 A1 * | 8/2008 |
| WO | WO 2008/133196 A1 | 11/2008 |

OTHER PUBLICATIONS

Ishii, Tatsuro, et al., "Clinical Evaluation of Bullet-Shaped Atelocollagen Sponge (Teruplug) as Protective Material for Tooth Extraction Wounds", Dental Outlook, 2001, pp. 665-677, vol. 97, No. 3.
Kim, Chang-Sung, et al., "Ectopic bone formation associated wtih recombinant human bone morphogenetic proteins-2 using absorbable collagen sponge and beta tricalcium phosphate as carriers", Biomaterials, 2005, pp. 2501-2507, vol. 26.
Tabata, Yasuhiko, et al., "Bone regeneration by basic fibroblast growth factor complexed with biodegradable hydrogels", Biomaterials, 1998, pp. 807-815, vol. 19.
Tabata, Yasuhiko, Ph.D., et al., "Skull bone regeneration in primates in response to basic fibroblast growth factor", Journal of Neurosurgery, Nov. 1999, pp. 851-856, vol. 91.
English Translation of the International Preliminary Report on Patentability mailed Apr. 19, 2012 for International Application No. PCT/JP2010/065108.
International Preliminary Report on Patentability mailed Mar. 15, 2012 for International Application No. PCT/JP2010/065108.
Extended Search Report issued in corresponding European Patent Application No. 10813797.7 on Mar. 6, 2013.
Yoshitake Takahashi et al., "Enhanced osteoinduction by controlled release of bone morphogenetic protein-2 from biodegradable sponge composed of gelatin and β-tricalcium phosphate", Biomaterials, 2005, 26: 4856-4865.
Yoshitake Takahashi et al., "Osteogenic differentiation of mesenchymal stem cells in biodegradable sponges composed of gelatin and β-tricalcium phosphate", Biomaterials, 2005, 26: 3587-3596.
Ju-Ha Song et al., "Bioactive and degradable hybridized nanofibers of gelatin-siloxane for bone regeneration", J. Biomed. Mater. Res., 2008, 84A: 875-884.
Yong Pan et al., "Demineralized bone matrix gelatin as scaffold for tissue engineering", African Journal of Microbiology Research, 2010, 4(9): 865-870.
Office Action issued in corresponding European Patent Application No. 10813797.7, dated Nov. 27, 2013.
Decision of Rejection, dated Jul. 30, 2014, issued by the State Intellectual Property Office of the People's Republic of China, in counterpart Chinese Patent Application No. 201080039114.7.
Office Action issued in counterpart Chinese Patent Application No. 201080039114.7, dated Mar. 17, 2014.

(Continued)

*Primary Examiner* — Xiaozhen Xie
(74) *Attorney, Agent, or Firm* — Sughrue Mion, PLLC

(57) ABSTRACT

It is an object of the present invention to provide a bone regeneration agent and a bone supplementation formulation, in which a supplementation material itself is capable of promoting bone regeneration. The present invention provides a bone regeneration agent which comprises a gelatin having an amino acid sequence derived from a partial amino acid sequence of collagen.

8 Claims, 5 Drawing Sheets
(2 of 5 Drawing Sheet(s) Filed in Color)

(56) References Cited

OTHER PUBLICATIONS

Office Action issued in counterpart Japanese Patent Application No. 2011-529950, dated Feb. 18, 2014.

Chinese Office Action, dated Sep. 3, 2013, issued in corresponding Chinese Application No. 201080039114.7.

Office Action, dated Oct. 28, 2014, issued by the European Patent Office in counterpart European Patent Application No. 10813797.7-1406.

* cited by examiner

SEQUENCE LISTING

<160> NUMBER OF SEQ ID NOS: 13

<210> SEQ ID NO 1
<211> LENGTH: 571
<212> TYPE: PRT
<213> ORGANISM: Artificial Sequence
<220> FEATURE:
<223> OTHER INFORMATION: Synthetic polypeptide

<400> SEQUENCE: 1

```
Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
            85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
            165                 170                 175

Asp Gly Ala Pro Gly Lys Asp Gly Val Arg Gly Leu Ala Gly Pro Pro
        180                 185                 190

Gly Ala Pro Gly Leu Gln Gly Ala Pro Gly Leu Gln Gly Met Pro Gly
    195                 200                 205

Glu Arg Gly Ala Ala Gly Leu Pro Gly Pro Lys Gly Glu Arg Gly Asp
210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
            245                 250                 255

Glu Arg Gly Asp Ala Gly Pro Lys Gly Ala Asp Gly Ala Pro Gly Lys
        260                 265                 270

Asp Gly Val Arg Gly Leu Ala Gly Pro Ile Gly Pro Pro Gly Glu Arg
    275                 280                 285

Gly Ala Ala Gly Leu Pro Gly Pro Lys Gly Glu Arg Gly Asp Ala Gly
290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
            325                 330                 335

Gly Leu Gln Gly Met Pro Gly Glu Arg Gly Ala Ala Gly Leu Pro Gly
        340                 345                 350

Pro Lys Gly Glu Arg Gly Asp Ala Gly Pro Lys Gly Ala Asp Gly Ala
    355                 360                 365

Pro Gly Lys Asp Gly Val Arg Gly Leu Ala Gly Pro Pro Gly Ala Pro
370                 375                 380

Gly Leu Gln Gly Ala Pro Gly Leu Gln Gly Met Pro Gly Glu Arg Gly
385                 390                 395                 400
```

-continued

```
Ala Ala Gly Leu Pro Gly Pro Lys Gly Glu Arg Gly Asp Ala Gly Pro
            405                 410                 415
Lys Gly Ala Asp Gly Ala Pro Gly Ala Pro Gly Leu Gln Gly Met Pro
        420                 425                 430
Gly Glu Arg Gly Ala Ala Gly Leu Pro Gly Pro Lys Gly Glu Arg Gly
    435                 440                 445
Asp Ala Gly Pro Lys Gly Ala Asp Gly Ala Pro Gly Lys Asp Gly Val
    450                 455                 460
Arg Gly Leu Ala Gly Pro Ile Gly Pro Pro Gly Glu Arg Gly Ala Ala
465                 470                 475                 480
Gly Leu Pro Gly Pro Lys Gly Glu Arg Gly Asp Ala Gly Pro Lys Gly
                485                 490                 495
Ala Asp Gly Ala Pro Gly Lys Asp Gly Val Arg Gly Leu Ala Gly Pro
            500                 505                 510
Ile Gly Pro Pro Gly Pro Ala Gly Ala Pro Gly Ala Pro Gly Leu Gln
        515                 520                 525
Gly Met Pro Gly Glu Arg Gly Ala Ala Gly Leu Pro Gly Pro Lys Gly
    530                 535                 540
Glu Arg Gly Asp Ala Gly Pro Lys Gly Ala Asp Gly Ala Pro Gly Lys
545                 550                 555                 560
Asp Gly Val Arg Gly Leu Ala Gly Pro Pro Gly
                565                 570

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 2

Asp Arg Gly Asp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Arg Glu Asp Val
1

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 4

Tyr Ile Gly Ser Arg
1               5

<210> SEQ ID NO 5
<211> LENGTH: 5
<212> TYPE: PRT
<213> ORGANISM: Artificial Sequence
<220> FEATURE:
```

```
<223> OTHER INFORMATION: Synthetic polypeptide

<400> SEQUENCE: 5

Pro Asp Ser Gly Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 6

Arg Tyr Val Val Leu Pro Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 7

Leu Gly Thr Ile Pro Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 8

Arg Asn Ile Ala Glu Ile Ile Lys Asp Ile
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 9

Ile Lys Val Ala Val
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 10

Asp Gly Glu Ala
1

<210> SEQ ID NO 11
<211> LENGTH: 4
<212> TYPE: PRT
<213> ORGANISM: Artificial Sequence
<220> FEATURE:
<223> OTHER INFORMATION: Synthetic polypeptide
```

<400> SEQUENCE: 11

Glu Arg Gly Asp
1

<210> SEQ ID NO 12
<211> LENGTH: 571
<212> TYPE: PRT
<213> ORGANISM: Artificial Sequence
<220> FEATURE:
<223> OTHER INFORMATION: Synthetic polypeptide
<220> FEATURE:
<221> NAME/KEY: Unsure
<222> LOCATION: (5),(6),(8),(9),(11),(12),(14),(15),(17),(18),(20),(21),
    (23),(24),(26),(27),(29),(30),(32),(33),(35),(36),(38),(39),
    (41),(42),(44),(45),(47),(48),(50),(51),(53),(54),(56),(57),
    (59),(60),(62),(63),(65),(66),(68),(69),(71),(72),(74),(75),
    (77),(78),(80),(81),(83),(84),(86),(87),(89),(90),(92),(93),
    (95),(96),(98),(99),(101),(102),(104),(105),(107),(108),(110),
    (111),(113),(114),(116),(117),(119),(120),(122),(123),(125),
    (126),(128),(129),(131),(132),(134),(135),(137),(138),(140),
    (141),(143),(144),(146),(147),(149),(150),(152),(153),(155),
    (156),(158),(159),(161),(162),(164),(165),(167),(168),(170),
    (171),(173),(174),(176),(177),(179),(180),(182),(183),(185),
    (186),(188),(189),(191),(192),(194),(195),(197),(198),(200),
    (201),(203),(204),(206),(207),(209),(210),(212),(213),(215),
    (216),(218),(219),(221),(222),(224),(225),(227),(228),(230),
    (231),(233),(234),(236),(237),(239),(240),(242),(243),(245),
    (246),(248),(249),(251),(252),(254),(255),(257),(258),(260),
    (261),(263),(264),(266),(267),(269),(270),(272),(273),(275),
    (276),(278),(279),(281),(282),(284),(285),(287),(288),(290),
    (291),(293),(294),(296),(297),(299),(300),(302),(303),(305),
    (306),(308),(309),(311),(312),(314),(315),(317),(318),(320),
    (321),(323),(324),(326),(327),(329),(330),(332),(333),(335),
    (336),(338),(339),(341),(342),(344),(345),(347),(348),(350),
    (351),(353),(354),(356),(357),(359),(360),(362),(363),(365),
    (366),(368),(369),(371),(372),(374),(375),(377),(378),(380),
    (381),(383),(384),(386),(387),(389),(390),(392),(393),(395),
    (396),(398),(399),(401),(402),(404),(405),(407),(408),(410),
    (411),(413),(414),(416),(417),(419),(420),(422),(423),(425),
    (426),(428),(429),(431),(432),(434),(435),(437),(438),(440),
    (441),(443),(444),(446),(447),(449),(450),(452),(453),(455),
    (456),(458),(459),(461),(462),(464),(465),(467),(468),(470),
    (471),(473),(474),(476),(477),(479),(480),(482),(483),(485),
    (486),(488),(489),(491),(492),(494),(495),(497),(498),(500),
    (501),(503),(504),(506),(507),(509),(510),(512),(513),(515),
    (516),(518),(519),(521),(522),(524),(525),(527),(528),(530),
    (531),(533),(534),(536),(537),(539),(540),(542),(543),(545),
    (546),(548),(549),(551),(552),(554),(555),(557),(558),(560),
    (561),(563),(564),(566),(567),(569),(570)
<223> OTHER INFORMATION: any amino acid

<400> SEQUENCE: 12

Gly Ala Pro Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
                20                  25                  30

Xaa Gly Xaa Xaa Gly Xaa Xaa Gly Xaa Xaa Gly Xaa Xaa Gly Xaa Xaa
            35                  40                  45

Gly Xaa Xaa Gly Xaa Xaa Gly Xaa Xaa Gly Xaa Xaa Gly Xaa Xaa Gly
50                  55                  60

Xaa Xaa Gly Xaa Xaa Gly Xaa Xaa Gly Xaa Xaa Gly Xaa Xaa Gly Xaa
65                  70                  75                  80

Xaa Gly Xaa Xaa Gly Xaa Xaa Gly Xaa Xaa Gly Xaa Xaa Gly Xaa Xaa
                85                  90                  95

Gly Xaa Xaa Gly Xaa Xaa Gly Xaa Xaa Gly Xaa Xaa Gly Xaa Xaa Gly
            100                 105                 110

Xaa Xaa Gly Xaa Xaa Gly Xaa Xaa Gly Xaa Xaa Gly Xaa Xaa Gly Xaa
            115                 120                 125

-continued

Xaa Gly Xaa Xaa Gly Xaa Xaa Gly Xaa Xaa Gly Xaa Xaa
    130                 135                 140

Gly Xaa Xaa Gly Xaa Xaa Gly Xaa Xaa Gly Xaa Xaa Gly
145                 150                 155                 160

Xaa Xaa Gly Xaa Xaa Gly Xaa Xaa Gly Xaa Xaa Gly Xaa
            165                 170                 175

Xaa Gly Xaa Xaa Gly Xaa Xaa Gly Xaa Xaa Gly Xaa Xaa
        180                 185                 190

Gly Xaa Xaa Gly Xaa Xaa Gly Xaa Xaa Gly Xaa Xaa Gly
    195                 200                 205

Xaa Xaa Gly Xaa Xaa Gly Xaa Xaa Gly Xaa Xaa Gly Xaa
    210                 215                 220

Xaa Gly Xaa Xaa Gly Xaa Xaa Gly Xaa Xaa Gly Xaa Xaa
225                 230                 235                 240

Gly Xaa Xaa Gly Xaa Xaa Gly Xaa Xaa Gly Xaa Xaa Gly
            245                 250                 255

Xaa Xaa Gly Xaa Xaa Gly Xaa Xaa Gly Xaa Xaa Gly Xaa
        260                 265                 270

Xaa Gly Xaa Xaa Gly Xaa Xaa Gly Xaa Xaa Gly Xaa Xaa
    275                 280                 285

Gly Xaa Xaa Gly Xaa Xaa Gly Xaa Xaa Gly Xaa Xaa Gly
290                 295                 300

Xaa Xaa Gly Xaa Xaa Gly Xaa Xaa Gly Xaa Xaa Gly Xaa
305                 310                 315                 320

Xaa Gly Xaa Xaa Gly Xaa Xaa Gly Xaa Xaa Gly Xaa Xaa
            325                 330                 335

Gly Xaa Xaa Gly Xaa Xaa Gly Xaa Xaa Gly Xaa Xaa Gly
        340                 345                 350

Xaa Xaa Gly Xaa Xaa Gly Xaa Xaa Gly Xaa Xaa Gly Xaa
    355                 360                 365

Xaa Gly Xaa Xaa Gly Xaa Xaa Gly Xaa Xaa Gly Xaa Xaa
    370                 375                 380

Gly Xaa Xaa Gly Xaa Xaa Gly Xaa Xaa Gly Xaa Xaa Gly
385                 390                 395                 400

Xaa Xaa Gly Xaa Xaa Gly Xaa Xaa Gly Xaa Xaa Gly Xaa
            405                 410                 415

Xaa Gly Xaa Xaa Gly Xaa Xaa Gly Xaa Xaa Gly Xaa Xaa
        420                 425                 430

Gly Xaa Xaa Gly Xaa Xaa Gly Xaa Xaa Gly Xaa Xaa Gly
    435                 440                 445

Xaa Xaa Gly Xaa Xaa Gly Xaa Xaa Gly Xaa Xaa Gly Xaa
    450                 455                 460

Xaa Gly Xaa Xaa Gly Xaa Xaa Gly Xaa Xaa Gly Xaa Xaa
465                 470                 475                 480

Gly Xaa Xaa Gly Xaa Xaa Gly Xaa Xaa Gly Xaa Xaa Gly
            485                 490                 495

Xaa Xaa Gly Xaa Xaa Gly Xaa Xaa Gly Xaa Xaa Gly Xaa
        500                 505                 510

Xaa Gly Xaa Xaa Gly Xaa Xaa Gly Xaa Xaa Gly Xaa Xaa
    515                 520                 525

Gly Xaa Xaa Gly Xaa Xaa Gly Xaa Xaa Gly Xaa Xaa Gly
    530                 535                 540

```
Xaa Xaa Gly Xaa Xaa Gly Xaa Xaa Gly Xaa Xaa Gly Xaa
545                 550                 555                 560

Xaa Gly Xaa Xaa Gly Xaa Xaa Gly Xaa Xaa Gly
                565                 570

<210> SEQ ID NO 13
<211> LENGTH: 571
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (192)..(192)
<223> OTHER INFORMATION: Xaa is any amino acid
<220> FEATURE:
<221> NAME/KEY: misc_feature
<222> LOCATION: (381)..(381)
<223> OTHER INFORMATION: Xaa is Asn or Glu
<220> FEATURE:
<221> NAME/KEY: misc_feature
<222> LOCATION: (570)..(570)
<223> OTHER INFORMATION: Xaa is any amino acid

<400> SEQUENCE: 13

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
    130                 135                 140

Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Xaa
            180                 185                 190

Gly Ala Pro Gly Leu Gln Gly Ala Pro Gly Leu Gln Gly Met Pro Gly
        195                 200                 205

Glu Arg Gly Ala Ala Gly Leu Pro Gly Pro Lys Gly Glu Arg Gly Asp
    210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
            260                 265                 270
```

```
Asp Gly Val Arg Gly Leu Ala Gly Pro Ile Gly Pro Pro Gly Glu Arg
            275                 280                 285

Gly Ala Ala Gly Leu Pro Gly Pro Lys Gly Glu Arg Gly Asp Ala Gly
        290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
            340                 345                 350

Pro Lys Gly Glu Arg Gly Asp Ala Gly Pro Lys Gly Ala Asp Gly Ala
            355                 360                 365

Pro Gly Lys Asp Gly Val Arg Gly Leu Ala Gly Pro Xaa Gly Ala Pro
        370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
            420                 425                 430

Gly Glu Arg Gly Ala Ala Gly Leu Pro Gly Pro Lys Gly Glu Arg Gly
            435                 440                 445

Asp Ala Gly Pro Lys Gly Ala Asp Gly Ala Pro Gly Lys Asp Gly Val
            450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
            500                 505                 510

Ile Gly Pro Pro Gly Pro Ala Gly Ala Pro Gly Ala Pro Gly Leu Gln
            515                 520                 525

Gly Met Pro Gly Glu Arg Gly Ala Ala Gly Leu Pro Gly Pro Lys Gly
            530                 535                 540

Glu Arg Gly Asp Ala Gly Pro Lys Gly Ala Asp Gly Ala Pro Gly Lys
545                 550                 555                 560

Asp Gly Val Arg Gly Leu Ala Gly Pro Xaa Gly
            565                 570
```

BONE REGENERATION AGENT COMPRISING GELATIN

CROSS REFERENCE TO RELATED APPLICATIONS

This application is a National Stage of International Application No. PCT/JP2010/065108 filed Sep. 3, 2010, claiming priority based on Japanese Patent Application Nos. 2009-204218 filed Sep. 4, 2009, and 2010-196678 filed Sep. 2, 2010, the contents of all of which are incorporated herein by reference in their entirety.

TECHNICAL FIELD

The present invention relates to a bone regeneration agent and a bone supplementation formulation, both of which comprise gelatin.

BACKGROUND ART

Body tissues are mainly composed of cells and extracellular matrixes (polymer structures). Extracellular matrixes which are secreted from cells provide hydrated spaces in which cells act or cell scaffoldings. In addition, extracellular matrixes function as storage houses for various growth factors secreted from cells, and have a profound influence on expression of cell functions or cell differentiation. Complicated interaction between extracellular matrixes and cells in a living body has an influence on various vital activities.

In recent years, highly advanced medical technology, whereby severe diseases are treated using artificial organs, gene therapy and regenerative medicine, has achieved remarkable success at clinical sites, and it has attracted global attention. Among others, regenerative medicine, whereby damaged tissues or organs are regenerated using three main elements, namely, cells, growth factors and extracellular matrixes that play main roles in tissue regeneration, has drawn attention as a treatment method for future generation. As a matter of fact, such regenerative medicine has already been realized for cultured skins or corneas.

Bone regeneration in the field of orthopedics or dentistry has attracted a great attention as an example of application of regenerative medicine. That is to say, when bone disease is developed in legs or lumbar parts, it causes abasia. When such bone disease is developed in tooth sections, it makes dietary intake difficult. Thus, bone disease is considered to cause a significant decrease in QOL. At present, representative examples of a known bone regeneration therapeutic formulation include: Infuse (a combination of BMP-2 with a collagen sponge) for treating spinal injuries; and BioOss (deproteinized, crushed cow bones), Puros (crushed human bone products), Gem21 (PDGF and βTCP), Osferion (βTCP) and Teruplug (Name used in the U.S.A.: FOUNDATION; a collagen sponge) used as bone supplementation agents for regenerating alveolar bones. Properties known to be necessary for bone regeneration therapeutic formulations include: 1. strength for maintaining structures; 2. the securement of spaces for bone regeneration; 3. cell scaffoldings for bone regeneration; 4. differentiation and growth of cells necessary for bone regeneration; and 5. degradability attended with bone regeneration.

In the dental field, representative diseases, for which the above-mentioned bone regeneration therapeutic formulations are known to be used, include: 1. ridge augmentation; 2. socket preservation; 3. periodontal bone defect regeneration; 4. implantable bone regeneration; and 5. sinus lift. The importance of scaffolding materials for promoting bone regeneration in the aforementioned diseases has been recognized. However, under the current circumstances, the aforementioned formulations rely on the bone regeneration ability of an agent (BMP or RDGF) contained therein. Such scaffolding materials have been believed to function as products for ensuring a space (strength) in an affected area. In many cases, inorganic materials have been widely used as such scaffolding materials.

In general, a collagen or a gelatin which is a denatured product of the collagen has been widely used as a scaffolding material (organic material) in regenerative medicine in many cases. It has been known that a highly oriented collagen plays an important role as a bone regeneration material in calcification (Non Patent Document 1). Thus, a sponge made of collagen has been placed on the market as a bone regeneration material (Teruplug (FOUDATION; Olympus Terumo Biomaterials Corp.)). However, a bone supplementation material using a collagen sponge provides only a scaffolding for tissue formation, and a single use of such a collagen sponge is not able to form a bone (Non Patent Document 2). Moreover, according to previous findings, a gelatin which is a denatured product of collagen has never been known to have a bone regeneration effect. Regarding gelatin, it is described that 1. a single use of a gelatin sponge inhibits bone regeneration (Non Patent Document 3), and that 2. a gelatin has bone regeneration ability that is lower than that of a collagen (Non Patent Document 4). Furthermore, it has been reported that no bones are formed in β-TCP that is an artificial bone ingredient, as with a gelatin sponge prepared by performing a heat treatment on a collagen (Non Patent Documents 2 and 5). As described above, it has been recognized that a gelatin that has been widely used as a base material in regenerative medicine is not suitable as a scaffolding material for bone regeneration therapeutic agents. With regard to a supplementation material that cannot form a bone by itself, a method for impregnating the supplementation material with a platelet-derived growth factor (PDGF) or a bone morphogenetic protein (BMP) which is a physiologically active substance has been studied (Patent Document 1). However, since a purified protein of such physiologically active substance is expensive, it has not yet been widely used.

On the other hand, biological polymers such as a gelatin have been broadly used as medical materials. As a result of the advancement of genetic engineering technology in recent years, a protein has been synthesized by introducing a gene into *Escherichia coli* or yeast. By this method, various types of recombinant collagen-like proteins have been synthesized (for example, Patent Documents 2 and 3). Such recombinant collagen-like proteins are more advantageous than natural gelatins in that they are excellent in terms of non-infectivity and uniformity, and in that since their sequences have been determined, the strength and degradability thereof can be precisely designed. However, the intended use of the recombinant gelatin, which has been proposed so far, is only the use as an alternative material of a natural gelatin. Naturally, the intended use of the recombinant gelatin as a bone regeneration agent has not been known.

PRIOR ART DOCUMENTS

Patent Documents

[Patent Document 1] JP Patent Publication (Kokai) No. 2004-203829
[Patent Document 2] U.S. Pat. No. 6,992,172
[Patent Document 3] WO 2008/103041

Non Patent Documents

[Non Patent Document 1] Tabata et al., Biomaterials 19, 807-815, 1998.
[Non Patent Document 2] Biomaterials 26: 2501-2507, 2005
[Non Patent Document 3] Tabata et al., Journal of Neurosurgery 91, 851-856, 1999
[Non Patent Document 4] Ishii et al., *Shika-i Tenbou* (Prospects for Dentists), 97(3), 665-677, 2001
[Non Patent Document 5] J Neurosurg 91: 851-856, 1999

SUMMARY OF INVENTION

Object to be Solved by the Invention

It is an object to be solved by the present invention to provide a bone regeneration agent and a bone supplementation formulation, in which a supplementation material itself is capable of promoting bone regeneration.

Means for Solving the Object

As a result of intensive studies directed towards achieving the aforementioned object, the present inventors have found that a gelatin having an amino acid sequence derived from a partial amino acid sequence of collagen, and more preferably a recombinant gelatin has an action to regenerate bone, thereby completing the present invention.

Thus, the present invention provides a bone regeneration agent which comprises a gelatin having an amino acid sequence derived from a partial amino acid of collagen.

Preferably, the gelatin having an amino acid sequence derived from a partial amino acid of collagen is a recombinant gelatin.

Preferably, the gelatin comprises repeats of a sequence represented by Gly-X-Y characteristic to collagen and has a molecular weight of 2 KDa to 100 KDa. wherein X and Y each independently represent an amino acid and a plurality of Gly-X-Y sequences may be the same or different.

Preferably, the gelatin comprises repeats of a sequence represented by Gly-X-Y characteristic to collagen and has a molecular weight of 10 KDa to 90 KDa. wherein X and Y each independently represent an amino acid and a plurality of Gly-X-Y sequences may be the same or different.

Preferably, the gelatin comprises repeats of a sequence represented by Gly-X-Y characteristic to collagen and has two or more sequences of cell adhesion signals in a single molecule wherein X and Y each independently represent an amino acid and a plurality of Gly-X-Y sequences may be the same or different.

Preferably, the cell adhesion signal sequence is an amino acid sequence represented by Arg-Gly-Asp.

Preferably, the amino acid sequence of the gelatin does not comprise any of serine and threonine.

Preferably, the amino acid sequence of the gelatin does not comprise any of serine, threonine, asparagine, tyrosine, and cysteine.

Preferably, the amino acid sequence of the gelatin does not comprise an amino acid sequence represented by Asp-Arg-Gly-Asp (SEQ ID NO: 2).

Preferably, the gelatin is represented by the following formula:

A-[(Gly-X-Y)$_n$]$_m$-B wherein A represents any amino acid or amino acid sequence, B represents any amino acid or amino acid sequence, there exist n amino acids each independently represented by X, there exist n amino acids each independently represented by Y, n represents an integer from 3 to 100, m represents an integer of 2 to 10, and n Gly-X-Y sequences may be the same or different.

Preferably, the gelatin is represented by the following formula:

Gly-Ala-Pro-[(Gly-X-Y)$_{63}$]$_3$-Gly     (SEQ ID NO: 12)

wherein there exist 63 amino acids each independently represented by X, there exist 63 amino acids each independently represented by Y, and 63 Gly-X-Y sequences may be the same or different.

Preferably, the gelatin has the following (1) or (2):
(1) the amino acid sequence shown in SEQ ID NO: 1; or
(2) an amino acid sequence having 80% or more homology to the amino acid sequence shown in SEQ ID NO: 1 and having an action to regenerate bone.

Preferably, the gelatin is crosslinked

Preferably, the crosslinking is carried out using an aldehyde, condensing agent or enzyme.

The present invention further provides a bone supplementation formulation which comprises the aforementioned bone regeneration agent of the present invention.

The present invention further provides a method for inducing bone regeneration which comprises administering a gelatin having an amino acid sequence derived from a partial amino acid of collagen to a subject in need of bone regeneration.

The present invention further provides a use of a gelatin having an amino acid sequence derived from a partial amino acid of collagen, for the production of a bone regeneration agent or a bone supplementation formulation.

Effect of the Invention

The bone regeneration agent of the present invention is capable of exhibiting an excellent bone regeneration effect by a supplementation material itself, without using a physiologically active substance such as a platelet-derived growth factor or a bone morphogenetic protein.

BRIEF DESCRIPTION OF DRAWINGS

The patent or application file contains at least one drawing executed in color. Copies of this patent or patent application publication with color drawings will be provided by the Office upon request and payment of the necessary fee.

EMBODIMENTS FOR CARRYING OUT THE INVENTION

Figure 1:
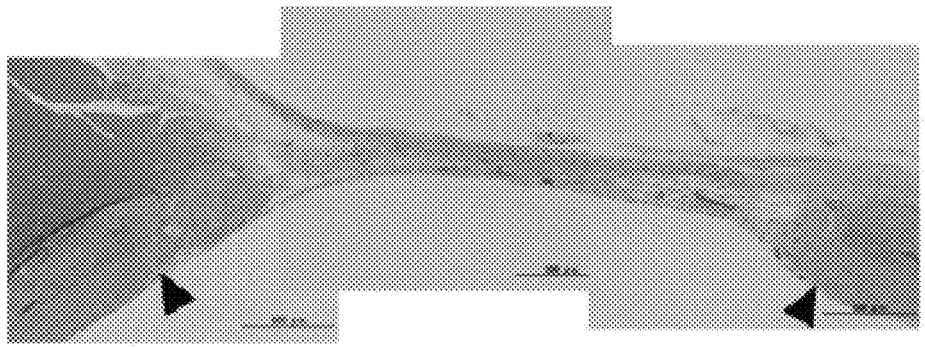
FIG. 1 is a HE stained image of an untreated rat calvarial bone-deficient model.

Hereinafter the embodiments of the present invention will be described in detail.

In the present invention, a gelatin having an amino acid sequence derived from a partial amino acid sequence of collagen is used as a bone regeneration agent. The bone regeneration agent of the present invention is characterized in that a gelatin having an amino acid sequence derived from a partial amino acid sequence of collagen exhibits bone regeneration action by itself. Accordingly, it is not necessary for the bone regeneration agent of the present invention to comprise other substances having bone regeneration action, other than the gelatin having an amino acid sequence derived from a partial amino acid sequence of collagen. Thus, the bone regeneration agent of the present invention preferably does not comprise other substances having bone regeneration action, other than the above-described gelatin. Specifically, the bone regeneration agent of the present invention preferably consists of the gelatin having an amino acid sequence derived from a partial amino acid sequence of collagen. The type of the collagen is not particularly limited, as long as it is present in the nature. Preferred examples of the collagen include collagen types I, II, III, IV and V. More preferred examples of the collagen include collagen types I, II and III. In another embodiment, preferred origins of the collagen are preferably a human, a bovine, a pig, a mouse and a rat. It is more preferably a human.

The gelatin used herein is not particularly limited, so long as the gelatin has an amino acid sequence derived from a partial amino acid of collagen. Preferably, the gelatin contains Gly-X-Y characteristic to collagen. When gelatin/collagen is compared with other proteins in terms of the amino acid composition or sequence, the GXY sequence is characteristic to collagen and forms a highly specific partial structure. Glycine accounts for approximately one-third of the partial structure as a whole. Glycine is repeatedly found in the amino acid sequence at a rate of 1 out of every 3 amino acids. Glycine is the simplest amino acid. There are few restrictions to arrangement of the molecular chain of glycine and thus glycine highly contributes to regeneration of the helix structure upon gelatinization. An amino acid represented by X or Y is rich in imino acid (proline or oxyproline) and the imino acid accounts for 10% to 45% of the amino acid sequence as a whole.

The gelatin used in the present invention may be a gelatin which is derived from natural animal or may be a recombinant gelatin. When a gelatin which is derived from natural animal is used, the origin of the gelatin is not particularly limited. The origin may be any animal such as fish, bovine, pig or goat.

Among the above, it is preferred that the gelatin having an amino acid sequence derived from a partial amino acid of collagen is a recombinant gelatin. Since the recombinant gelatin is not derived from an animal but is an artificial gelatin, it is highly biocompatible supplementation material where exogenous infection is avoided.

As a recombinant gelatin that can be used in the present invention, a recombinant gelatin having an amino acid sequence derived from a partial amino acid sequence of collagen can be used. Examples of a recombinant gelatin that can be used include, but are not limited to, recombinant gelatins described in EP1014176A2, U.S. Pat. No. 6,992,172, WO2004-85473, and WO2008/103041. A recombinant gelatin preferably used as the recombinant gelatin of the present invention is described below.

The recombinant gelatin used in the present invention has original properties of naturally occurring gelatin and thus it is highly biocompatible. In addition, the recombinant gelatin is not directly obtained from natural sources and thus has no risk of causing BSE or the like. In this regard, it has an excellent property of being non-infectious. In addition, the recombinant gelatin used in the present invention is more homogenous than naturally occurring gelatin. Further, the recombinant gelatin has a predetermined sequence. Thus, it is possible to precisely design the recombinant gelatin in terms of strength and degradability with few errors by crosslinking or the like described below.

The molecular weight of the recombinant gelatin used in the present invention is preferably 2 KDa to 100 KDa, more preferably 2.5 KDa to 95 KDa, further preferably 5 KDa to 90 KDa, and most preferably 10 KDa to 90 KDa.

Preferably, the recombinant gelatin used in the present invention contains repeats of a sequence represented by Gly-X-Y characteristic to collagen. Here, a plurality of sequences each represented by Gly-X-Y may be the same or different. Gly in Gly-X-Y represents glycine. X and Y in Gly-X-Y represent any amino acids (and preferably any amino acids other than glycine). When gelatin/collagen is compared with other proteins in terms of the amino acid composition or sequence, the GXY sequence is characteristic to collagen and forms a highly specific partial structure. Glycine accounts for approximately one-third of the partial structure as a whole. Glycine is repeatedly found in the amino acid sequence at a rate of 1 out of every 3 amino acids. Glycine is the simplest amino acid. There are few restrictions to arrangement of the molecular chain of glycine and thus glycine highly contributes to regeneration of the helix structure upon gelatinization. Preferably, an amino acid represented by X or Y is rich in imino acid (proline or oxyproline) and the imino acid accounts for 10% to 45% of the amino acid sequence as a whole. Amino acids forming the GXY repeat structure account for preferably 80% or more, more preferably 95% or more, and most preferably 99% or more of the amino acid sequence as a whole.

A generally available gelatin contains charged polar amino acids and uncharged polar amino acids at a ratio of 1:1. Here, the term "polar amino acid" specifically refers to cysteine, aspartic acid, glutamic acid, histidine, lysine, asparagine, glutamine, serine, threonine, tyrosine, or arginine. In particular, the term "uncharged polar amino acid" refers to cysteine, asparagine, glutamine, serine, threonine, or tyrosine. The percentage of polar amino acids relative to all amino acids constituting the recombinant gelatin used in the present invention is 10% to 40% and preferably 20% to 30%. In addition, the percentage of uncharged polar amino acids relative to the polar amino acids is preferably 5% to less than 20% and more preferably less than 10%. Further, the amino acid sequence does not contain one amino acid and preferably two amino acids or more selected from among serine, threonine, asparagine, tyrosine, and cysteine.

In general, it is known that a polypeptide contains a minimal amino acid sequence that functions as a cell adhesion signal sequence (e.g., "Pathophysiology" (Byotai Seiri) Vol. 9, No. 7 (1990), p. 527, Nagai Shoten Co., Ltd.). It is preferable for a single molecule of the recombinant gelatin used in the present invention to have at least two cell adhesion signal sequences. Specifically, amino acids are shown by one-letter notation in a cell adhesion signal sequence. In view of an increase in types of adhering cells, examples of such sequence are: preferably an RGD sequence, an LDV sequence, an REDV (SEQ ID NO: 3) sequence, a YIGSR (SEQ ID NO: 4) sequence, a PDSGR (SEQ ID NO: 5) sequence, an RYVVLPR (SEQ ID NO: 6) sequence, an LGTIPG (SEQ ID NO: 7) sequence, an RNIAEIIKDI (SEQ ID NO: 8) sequence, an IKVAV (SEQ ID NO: 9) sequence, an LRE sequence, a DGEA (SEQ ID NO: 10) sequence, and an HAV sequence, more preferably an RGD sequence, a YIGSR (SEQ ID NO: 4) sequence, a PDSGR (SEQ ID NO: 5) sequence, an LGTIPG (SEQ ID NO: 7) sequence, an IKVAV (SEQ ID NO: 9) sequence, and an HAV sequence; and particularly preferably an RGD sequence. Among the RGD sequence, an ERGD (SEQ ID NO: 11) sequence is preferred.

In terms of arrangement of RGD sequences in the recombinant gelatin used in the present invention, the number of amino acids present between two RGD sequences is preferably 0 to 100 and more preferably 25 to 60. Preferably, the number of amino acids is not uniformly determined.

In view of cell adhesion/growth, the number of such minimal amino acid sequences in a single protein molecule is preferably 3 to 50, more preferably 4 to 30, particularly preferably 5 to 20, and most preferably 12.

The percentage of RGD motifs in the recombinant gelatin used in the present invention related to the total number of amino acids is preferably at least 0.4%. If the recombinant gelatin comprises 350 amino acids or more, each stretch of 350 amino acids contains preferably at least one RGD motif. The percentage of RGD motifs related to the total number of amino acids is more preferably at least 0.6%, further preferably at least 0.8%, still further preferably at least 1.0%, even further preferably at least 1.2%, and most preferably at least 1.5%. The number of RGD motifs in the recombinant gelatin is preferably at least 4, more preferably 6, further preferably 8, and even further preferably 12 to 16 per 250 amino acids. A percentage of RGD motifs of 0.4% corresponds to at least one RGD sequence per 250 amino acids. The number of RGD motifs is represented by an integer. Therefore, in order to achieve a percentage of RGD motifs of 0.4%, it is necessary for a gelatin comprising 251 amino acids to contain at least two RGD sequences. Preferably, the recombinant gelatin of the present invention contains at least 2 RGD sequences per 250 amino acids, more preferably at least 3 RGD sequences per 250 amino acids, and further preferably at least 4 RGD sequences per 250 amino acids. In another embodiment, the recombinant gelatin of the present invention comprises at least 4, preferably 6, more preferably 8, and further preferably 12 to 16 RGD motifs.

In addition, the recombinant gelatin may be partially hydrolyzed.

Preferably, the recombinant gelatin used in the present invention has a structure comprising repeats of A-[(Gly-X-Y)n]m-B. Here, "m" is an integer of preferably 2 to 10 and more preferably 3 to 5. In addition, "n" is an integer of preferably 3 to 100, more preferably 15 to 70, and most preferably 50 to 65.

Preferably, a plurality of naturally occurring collagen sequence units are bound to form a repeat unit. The term "naturally occurring collagen" used herein may refer to any naturally occurring collagen. However, preferable examples thereof include type-I, type-II, type-III, type-IV, and type-V collagens. More preferably, type-I, type-II, and type-III collagens are used. In another embodiment, the origin of such collagen is preferably a human, bovine, pig, mouse, or rat and it is more preferably a human.

The isoelectric point of the recombinant gelatin used in the present invention is preferably 5 to 10, more preferably 6 to 10, and further preferably 7 to 9.5.

Preferably, the recombinant gelatin is not deaminated.

Preferably, the recombinant gelatin is not procollagen or does not comprise procollagen.

Preferably, the recombinant gelatin does not comprise telopeptide.

Preferably, the recombinant gelatin is a substantially pure collagen material prepared from a nucleic acid encoding a naturally occurring collagen.

Particularly preferably, the recombinant gelatin used in the present invention is a recombinant gelatin having the following (1) or (2):

(1) the amino acid sequence shown in SEQ ID NO: 1; or (2) an amino acid sequence having 80% or more, more preferably 90% or more, and most preferably 95% or more homology to the amino acid sequence shown in SEQ ID NO: 1, and having an action to regenerate bone.

The recombinant gelatin used in the present invention can be produced by a gene recombination technique known to persons skilled in the art. For instance, it can be produced according to the method described in EP1014176A2, U.S. Pat. No. 6,992,172, WO2004/85473, or WO2008/103041. Specifically, a transformant is produced by obtaining a gene encoding the amino acid sequence of a predetermined recombinant gelatin, incorporating the gene into an expression vector to prepare a recombinant expression vector, and introducing the vector into an appropriate host. The obtained transformant is cultured in an appropriate medium to produce a recombinant gelatin. Therefore, the recombinant gelatin used in the present invention can be prepared by collecting the produced recombinant gelatin from the culture product.

The recombinant gelatin used in the present invention can be chemically modified depending on the application thereof. Chemical modification may be performed via introduction of a low molecular compound or a different polymer (e.g., a biopolymer (sugar or protein), a synthetic polymer, or polyamide) into a carboxyl group or an amino group of a side chain of the recombinant gelatin or crosslinking between recombinant gelatin chains. For example, a carbodiimide-based condensing agent is used for introduction of a low molecular compound into the gelatin.

The crosslinking agent used in the present invention is not particularly limited, as long as the present invention can be carried out. It may be a chemical crosslinking agent or an enzyme. Examples of a chemical crosslinking agent include formaldehyde, glutaraldehyde, carbodiimide, and cyanamide. Preferably, formaldehyde or glutaraldehyde is used. Further, crosslinking of a gelatin can be conducted by light irradiation to a gelatin into which a photoreactive group has been introduced, light irradiation under the presence of a photosensitizer, or the like. Examples of a photoreactive group include a cinnamyl group, a coumarin group, a dithiocarbamyl group, xanthene dye, and camphorquinone. Among the aforementioned crosslinking agent, glutaraldehyde is most preferred.

In a case in which enzymatic crosslinking is carried out, an enzyme used is not particularly limited, as long as it has an action of causing crosslinking between gelatin chains However, crosslinking can be carried out using preferably transglutaminase or laccase and most preferably transglutaminase. Examples of proteins that are enzymatically crosslinked by transglutaminase include, but are not particularly limited to, proteins having lysine residues and glutamine residues. A mammalian-derived or microorganism-derived transglutaminase may be used. Specific examples thereof include: the Activa series (produced by Ajinomoto Co., Inc.); commercially available mammalian-derived transglutaminases serving as reagents such as guinea pig liver-derived transglutaminase, goat-derived transglutaminase, and rabbit-derived transglutaminase (produced by Oriental Yeast Co., Ltd., Upstate USA Inc., Biodesign International, etc.); and a human-derived blood coagulation factor (Factor XIIIa, Haematologic Technologies, Inc.).

Crosslinking of the gelatin comprises the following two steps: a step of mixing a gelatin solution and a crosslinking agent; and a step of causing a reaction in the obtained homogenous solution.

According to the present invention, the mixing temperature for treating the gelatin with a crosslinking agent is not particularly limited, as long as the solution can be homogenously agitated. However, it is preferably 0° C. to 40° C., more preferably 0° C. to 30° C., further preferably 3° C. to 25° C., still further preferably 3° C. to 15° C., even further preferably 3° C. to 10° C., and particularly preferably 3° C. to 7° C.

After agitation of the gelatin and the crosslinking agent, the temperature can be increased. The reaction temperature is not particularly limited, as long as crosslinking can proceed. However, in view of denaturation or degradation of the gelatin, it is substantially 0° C. to 60° C., preferably 0° C. to 40° C., more preferably 3° C. to 25° C., further preferably 3° C. to 15° C., still further preferably 3° C. to 10° C., and particularly preferably 3° C. to 7° C.

In the present invention, the above-described gelatin having an amino acid sequence derived from a partial amino acid sequence of collagen is administered to a subject in need of bone regeneration (for example, a mammal such as a human), so that bone regeneration can be induced.

The bone regeneration agent of the present invention can be used as a bone supplementation formulation.

The dose, usage and dosage form of the bone regeneration agent and the bone supplementation formulation of the present invention can be determined, as appropriate, depending on the intended use thereof. For example, the bone regeneration agent of the present invention may be directly administered to a target site in a living body. Otherwise, the bone regeneration agent of the present invention may be suspended in a liquid excipient including an aqueous solvent such as a distilled water for injection, a normal saline for injection, or a buffer with pH 5 to 8 (a phosphate buffer, a citrate buffer, etc.), and it may be then administered by injection, coating, etc. Moreover, the bone regeneration agent of the present invention may be mixed with a suitable excipient so as to prepare an ointment, a gel, a cream, etc., and it may be then applied. That it to say, the administration form of the bone regeneration agent of the present invention may be either oral administration or parenteral administration (for example, intravenous administration, intramuscular administration, subcutaneous administration, intracutaneous administration, etc.).

Examples of the dosage form of the bone regeneration agent of the present invention include: oral administration agents such as a tablet, a powdery agent, a capsule, a granular agent, an extract or a syrup; and parenteral administration agents such as an injection (for example, intravenous injection, intramuscular injection, subcutaneous injection, intracutaneous injection, etc.).

Preferably, the bone regeneration agent and the bone supplementation formulation of the present invention can be directly administered to a bone defect site in a living body. Thus, when the bone regeneration agent of the present invention is locally administered, its form is not particularly specified. Examples of the form include a sponge, a film, a nonwoven fabric, a fiber (tube), a particle, and a mesh.

The bone regeneration agent and the bone supplementation formulation of the present invention can be prepared according to a method known to a person skilled in the art. For example, when the pharmaceutical carrier is a liquid, the bone regeneration agent and the bone supplementation formulation of the present invention can be dissolved or dispersed in the liquid. On the other hand, when the pharmaceutical carrier is a powder, the bone regeneration agent and the bone supplementation formulation of the present invention can be mixed with or adsorbed on the powders. Furthermore, the bone regeneration agent and the bone supplementation formulation of the present invention may also comprise pharmaceutically acceptable additives (for example, a preservative, a stabilizer, an antioxidant, an excipient, a binder, a disintegrator, a wetting agent, a lubricant, a coloring agent, an aromatic agent, a corrigent, a coating, a suspending agent, an emulsifier, a solubilizer, a buffer, an isotonizing agent, a plasticizer, a surfactant, a soothing agent, etc.), as necessary.

The dosage of the gelatin is not particularly limited. For example, it is 1 to 100 mg, and preferably 1 to 50 mg per $cm^2$ of surface area of a living body, to which the gelatin is administered.

Examples of a target disease, to which the bone regeneration agent and the bone supplementation formulation of the present invention is administered, include bone defect caused by external injury, oral surgery disease, osteoporosis, and arthropathy.

The present invention will be more specifically described in the following examples. However, these examples are not intended to limit the scope of the present invention.

EXAMPLES

As a recombinant gelatin, CBE3 (WO2008-103041) described below was prepared.
CBE3
Molecular weight: 51.6 kD
Structure: Gly-Ala-Pro[(Gly-X-Y)$_{63}$]$_3$Gly (SEQ ID NO: 12)
Number of amino acids: 571
Number of RGD sequences: 12
Imino acid content: 33%
Substantially 100% of amino acids form the Gly-X-Y repeat structure.
The amino acid sequence of CBE3 does not contain any of serine, threonine, asparagine, tyrosine, and cysteine.
CBE3 has the ERGD sequence.
Isoelectric point: 9.34
Amino acid sequence (SEQ ID NO: 1 in the Sequence Listing) (This amino acid sequence corresponds to the amino acid sequence shown in SEQ ID NO: 3 in WO2008/103041. Note that "X" at the end was modified to "P.")

GAP(GAPGLQGAPGLQGMPGERGAAGLPGPKGERGDAGPKGADGAPGAPG

LQGMPGERGAAGLPGPKGERGDAGPKGADGAPGKDGVRGLAGPIGPPGER

GAAGLPGPKGERGDAGPKGADGAPGKDGVRGLAGPIGPPGPAGAPGAPGL

QGMPGERGAAGLPGPKGERGDAGPKGADGAPGKDGVRGLAGPP)3G

In the Examples described below, the above CBE3 was used as the recombinant gelatin (which is referred to as R-Gel), unless otherwise specified.

Example 1

(1) Preparation of Recombinant Gelatin Gel

3% glutaraldehyde was added to a 10% recombinant gelatin aqueous solution to an amount of 1/10 of the total amount. The final concentration of glutaraldehyde was 0.3%. A mixed solution obtained by stirring the thus prepared solution was poured into a silicon frame (30 mm long×30 mm wide×2 mm high), and it was then left at rest at room temperature for 2 hours. Subsequently, the resultant was left at rest at 4° C. for 12 hours, so as to obtain a chemically cross-linked gelatin sheet. This gelatin sheet was immersed in an excessive amount of glycine aqueous solution for 1 hour, and unreacted glutaraldehyde or aldehyde groups were inactivated. Subsequently, the resultant was washed with distilled water twice and was then freeze-dried, so as to obtain a cross-linked recombinant gelatin gel. The freeze-dried recombinant gelatin gel was subjected to a crusher, New Power Mill (Osaka Chemical Co., LTD.), so as to obtain powders. The obtained powders were sterilized with ethylene oxide gas before being used for samples in animal experiments.

(2) Test Regarding Induction of Bone Regeneration in Rat Parietal Bone Defect Portions Ten SD rats (male, 10- to 12-week-old, 0.3 to 0.5 kg) were used as experimental animals. 0.8 ml/kg pentobarbital (Nembutal (registered trademark), Dainippon Sumitomo Pharma Co., Ltd.) was administered into the abdominal cavity of each rat to anesthetize them. The parietal bone of each rat was exposed, and a circular bone defect portion having a diameter of 5 mm was created. The thus created bone defect portion was filled with approximately 10 mg of the sterilized, recombinant gelatin gel, and the skin was then sutured.
Experiment Standard Groups:
Group 1: Only defect
Group 2: Recombinant gelatin gel (approximately 10 mg)
Group 3: Pig-derived gelatin (high grade gelatin, TYPE: APAT, Nippi Inc.) (approximately 10 mg)
Group 4: Collagen (Teruplug (trade name) crushed product, Olympus Terumo Biomaterials Corp.) (approximately 10 mg)
Group 5: Bovine cancellous bone (Bio-Oss (trade name), Osteohealth) (approximately 20 mg)

Figure 2:
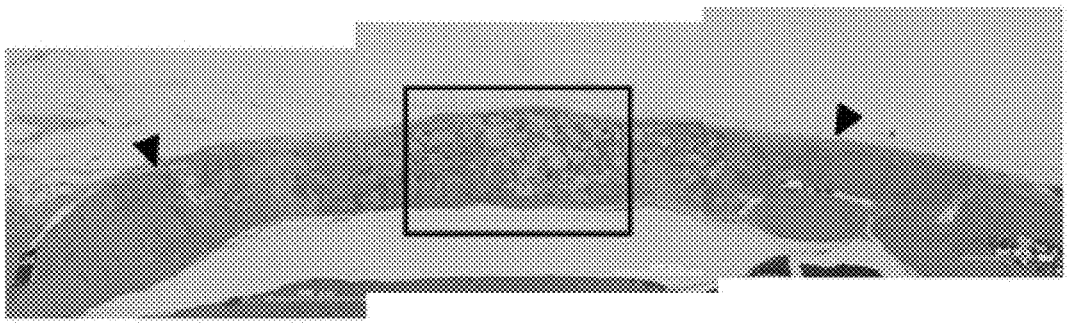
FIG. 2 is a HE stained image showing that recombinant gelatin powders were embedded in a defect portion and a bone was then formed in the affected area.
Figure 3:
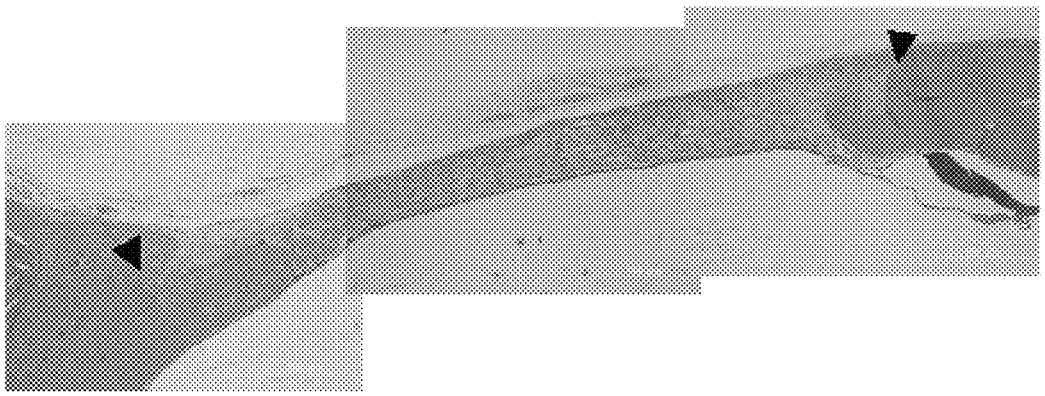
FIG. 3 is a HE stained image showing that pig-derived gelatin powders were embedded in a defect portion.
Figure 4:
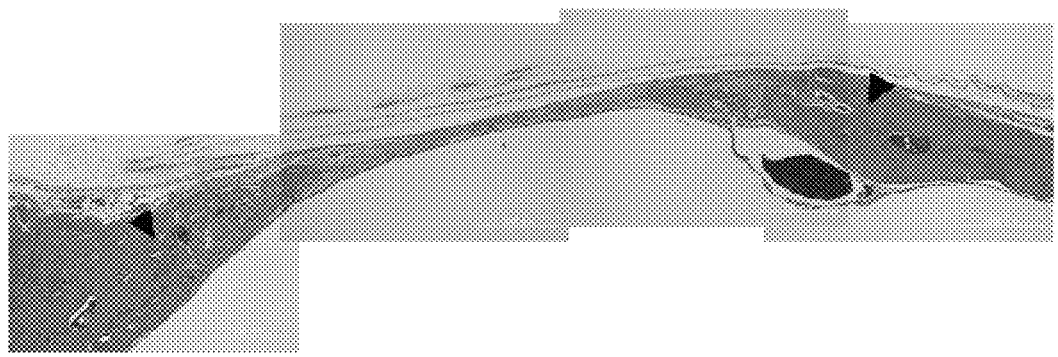
FIG. 4 is a HE stained image showing that collagen powders were embedded in a defect portion.
Figure 5:
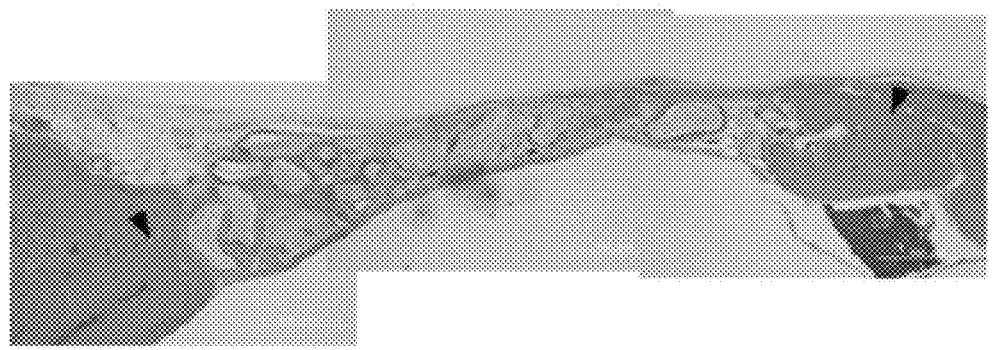
FIG. 5 is a HE stained image showing that a bovine cancellous bone Bio-Oss (trade name), Osteohealth) which is an insoluble substrate was embedded in a defect portion.

On the 4$^{th}$ week after performing the surgery, the rats were sacrificed by exsanguination under anesthesia with pentobarbital, and the heads thereof were extirpated. The parietal bone including the embedded portions was subjected to histological observation with HE staining.
(4) Results The observation results of Groups 1 to 5 are shown in FIGS. 1 to 5. In the case of using the pig-derived gelatin and the recombinant gelatin, significant induction of bone formation was observed (FIG. 2 and FIG. 3). Bone formation was not promoted by the collagen or a single use of the insoluble substrate (FIG. 4 and FIG. 5). However, using the recombinant gelatin of the present invention containing a large amount of RGD motif, bone formation was observed in a rat parietal bone defect portion by a single use of a bone supplementation material, which could not have formed bones so far (FIG. 2). This result demonstrated that effective bone formation can be carried out without using a physiologically active substance such as BMP that may cause side effects.

Example 2

Preparation of Recombinant Gelatin (R-Gel) and Animal Gelatin Formation

Figure 6:
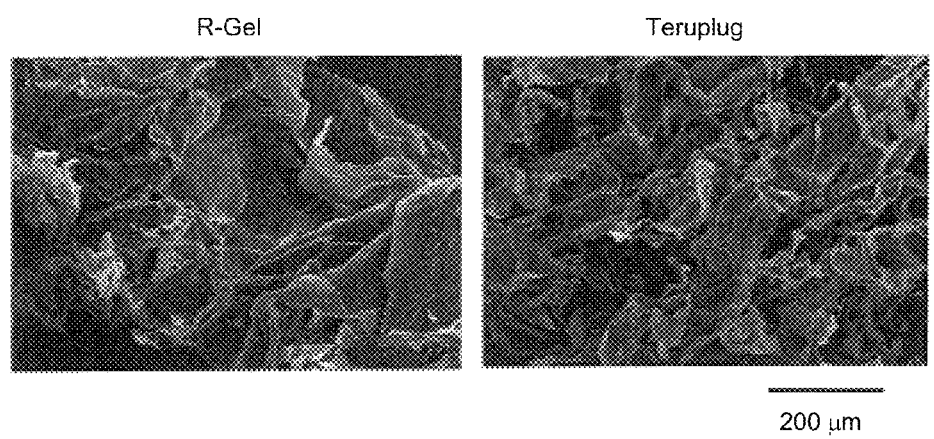
FIG. 6 shows electron micrographs of the insides of an R-Gel formulation and Teruplug.

An aqueous solution (pH 6) containing R-Gel or an animal gelatin (APAT, manufactured by Nippi Inc., concentration: 7.5%) and glutaraldehyde (GA, 0.3%) was intensively stirred, and the solution was stirred for 3 minutes while forming air bubbles. The obtained solution containing an infinite number of air bubbles was left at rest at 4° C. overnight, so as to obtain a gelatinous solid containing a large number of air bubbles. The obtained gel was washed with a 0.1 M glycine aqueous solution twice, unreacted glycine was inactivated, and the resultant was then washed with water four times. The gel that had been washed with water was freeze-dried to obtain a spongy R-Gel and gelatin gel. This sponge was crushed with a mill, so as to obtain spongy granules having a granular size of approximately several hundreds of μm. The internal structures of the granules and Teruplug were observed under a scanning electron microscope. As a result, it was found that they had the same porous structure (FIG. 6).

An ethylene oxide-sterilized product of the spongy granules was used in the following effectiveness evaluation. The R-Gel and animal gelatin that had been cross-linked by the GA were each transplanted into rats or dogs, and the effectiveness thereof was then evaluated.

Example 3

Preparation of Rat Cranial Bone-Deficient Models

In order to evaluate the bone regeneration ability of R-Gel, rat cranial bone-deficient models used as a bone regeneration ability evaluation system were used (Tissue Eng (2007) 13(3): 501-12). The cranial bone follows the same bone formation process (intramembranous ossification) as that of the alveolar bone. Thus, the cranial bone is generally used in evaluation of dental bone supplementation agents.

Figure 7:
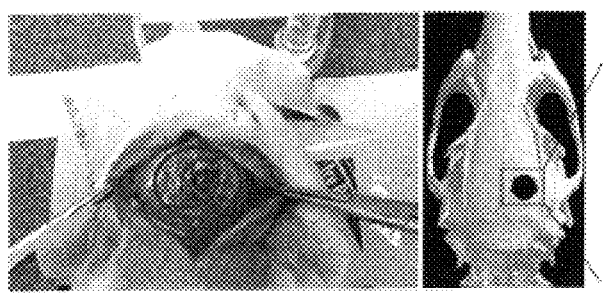
FIG. 7 shows rat cranial bone-deficient models. Left: a macroscopic photograph. Right: a µCT photograph (Micro-CT image: Tissue Eng (2007) 13(3): 501-12).
Figure 8:
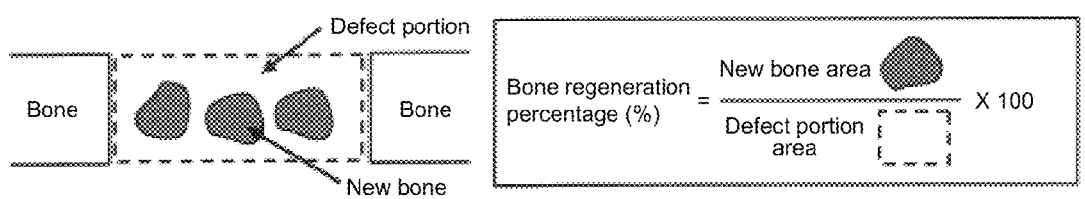
FIG. 8 shows a method for calculating a bone regeneration percentage (analyzed from pathological specimens).

Sprague-Dawley rats (SD rats, male, 10- to 12-week-old) were anesthetized, and a circular defect portion (diameter =5 mm) was created in the right-sided parietal bone using a drill (Osada Success 40, Osada Electric Co., Ltd.) (FIG. 7). Bone fragments and blood existing in the defect portion, which affected bone regeneration, were removed by washing them with a normal saline, and the skin of the affected area was then sutured. After a predetermined period of time (3 weeks, 1, 2 and 3 months) had passed, the rats were sacrificed by laparotomy and exsanguination. The defect portion of each rat was observed by the naked eye, and the head portion was fixed with formalin and decalcified. Thereafter, a section obtained by slicing a block embedded in paraffin was stained with hematoxylin and eosin (H & E), so as to prepare a specimen. The pathological specimen was observed under an optical microscope, and the ratio of a new bone to the defect portion was defined as a bone regeneration percentage (FIG. 8). Herein, the bone regeneration ability of the formulation was evaluated using such a bone regeneration percentage.

When the defect portion was observed, the defect portion of each rat was slightly dished, and almost the entire defect portion was covered with soft tissues. A small amount of white solid portion that seemed to be a new bone (regenerate bone) was observed around the cut section. When this specimen was observed under an optical microscope one month after performing the surgery, approximately 30% of the defect portion was covered with thin granulation tissues, and bone regeneration from existing bones was observed in approximately 10% of the defect portion. The bone regeneration percentage increased as the time passed. However, the percentage of the regenerate bone was approximately 30% even three months after performing the surgery. The amount of the bone regenerated was matched with the data of the publication (bone regeneration percentage for 3 months: approximately 30%) (Tissue Eng (2007) 13(3): 501-12), and thus, it was considered that a model system could be constructed.

Example 4

Evaluation of Bone Regeneration Percentage in Rat Cranial Bone Defect Portion

A R-Gel formulation, an animal gelatin formulation, Teruplug (Olympus Terumo Biomaterials Corp.) and Bio-Oss Cancellous (0.25 to 1 mm, Osteohealth) were each transplanted into the rat cranial bone defect portion created in Example 3. A collagen membrane (BioGide, Osteohealth) was placed on each of the R-Gel, animal gelatin and Bio-Oss Cancellous each having a dosage form that was a granular agent, so as to prevent the release of granules from the affected area. A group, to the affected area of which nothing had been applied, was defined as a control.

Figure 9:
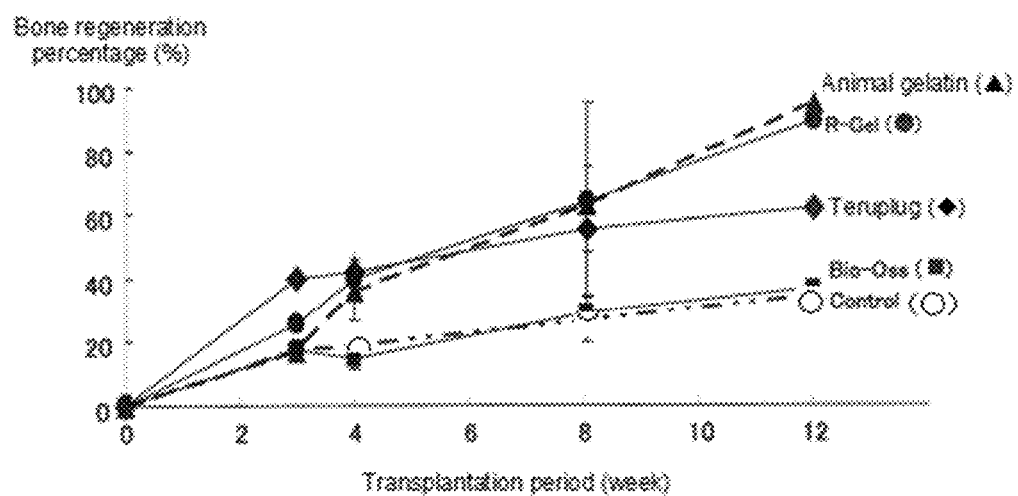
FIG. 9 shows a change over time in the bone regeneration percentage in a rat cranial bone-deficient portion. R-Gel and an animal gelatin exhibited bone regeneration percentages higher than those of Bio-Oss Cancellous and Teruplug.

The bone regeneration percentage of an affected area, to which the Bio-Oss Cancellous had been applied, was the same level as that of the control, and it remained about 30% three months after performing the surgery. In the case of the Teruplug that was a collagen sponge, a bone was regenerated over time, and approximately 60% of the affected area was repaired with the regenerate bone three months after performing the surgery (FIG. 9). On the other hand, in the case of the R-Gel and the animal gelatin, bone regeneration progressed at the same level as that of the Teruplug until one month after the transplantation, but thereafter, their bone regeneration levels became higher than that of the Teruplug, and approximately 90% of the affected area was repaired with the regenerate bone three months after the transplantation (wherein the bone regeneration percentage was 1.5 times higher than that in the case of the Teruplug). Accordingly, it can be said that the R-Gel and the animal gelatin spongy granules have bone regeneration ability that is higher than that of the Teruplug.

Example 5

Analysis of Pathological Specimens Using Animal Gelatin and R-Gel

Figure 10:
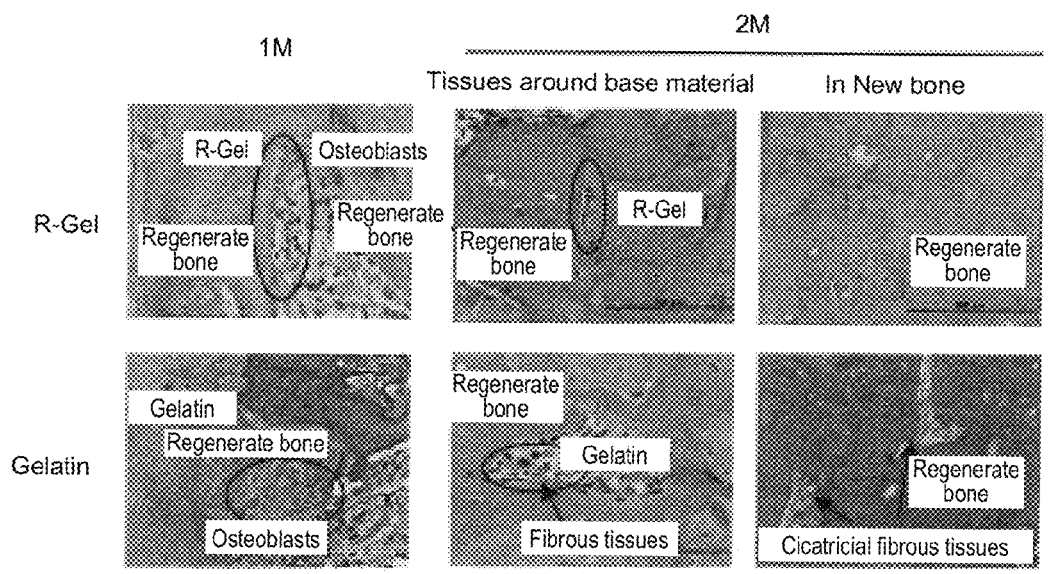
FIG. 10 shows pathological specimen photographs (H & E stained) taken one month and two months after transplantation of R-Gel and an animal gelatin into rat cranial bones. R-Gel (upper photographs) and the animal gelatin (lower photographs). One month after the transplantation, bones were regenerated on the surfaces of the R-Gel and the animal gelatin. Two months after the transplantation, bones were regenerated at sites around the R-Gel, in which the R-Gel had been decomposed by cells, and bones with a few voids were regenerated. On the other hand, around the animal gelatin, soft fibrous tissues were observed at sites in which the animal gelatin had been decomposed by cells, and a large number of cicatricial fibrous tissues were contained in the regenerated bones.

In order to analyze bone regeneration using an animal gelatin (gelatin) and a recombinant gelatin (R-Gel) more in detail, the forms of tissues around each base material and the tissues of a regenerate bone were analyzed (FIG. 10). One month after the transplantation, a large number of osteoblasts were found on the surfaces of both the R-Gel and gelatin base materials, and new bones were found. Thus, no significant difference was found between the tissue images of the two base materials.

Two months after the transplantation, the presence of a large number of osteoblasts, decomposition of the R-Gel by these cells, and formation of a new bone with a few defects were observed in voids formed between the R-Gel and the new bone. On the other hand, at the interface between animal gelatin and a new bone, a large number of fibroblasts, formation of fibrous soft tissues and a new bone containing a large number of cicatricial fibrous tissues were observed. That is, the R-Gel regenerated a bone that was more dense than that regenerated by the animal gelatin.

Example 6

Preparation of Dog Socket Preservation Model

A model was prepared according to the previous report (Araujo M et al. Int. J. Periodontics Restorative Dent. 28, 123-135, 2008.). Under anesthesia, the oral cavity of a beagle dog was disinfected with an Isodine solution, and the center between the second premolar (P2) and the third premolar (P3) in both mandibles was excised with a fissure bur. A periodontal ligament around teeth in the distal position was excised with a knife, and the teeth in the distal position were extracted using dental forceps and an elevator. The tooth extraction portion (wound socket after tooth extraction) was filled with a tampon that had been immersed in a 10-fold diluted solution of an adrenaline injection solution (Bosmin injection 1 mg/mL, Daiichi Sankyo Co., Ltd.) for hemostasis. The dental pulp of the remaining teeth in the proximal position was removed using a reamer, the pulp cavity was then filled with Gutta-percha, and it was then sealed with a pulp canal sealer.

Example 7

Evaluation of Effectiveness in Dog Model

The tooth extraction portion created in Example 6 was filled with BioOss Cancellous (0.25 to 1 mm, Osteohealth), Teruplug (Olympus Terumo Biomaterials Corp.), R-Gel, or an animal gelatin, up to the crest of the alveolar bone. A collagen membrane (Biogide, Osteohealth) was placed between the infills other than the Teruplug and the gingiva. In the case of a control, such an infill and a membrane were not placed.

Figure 11:
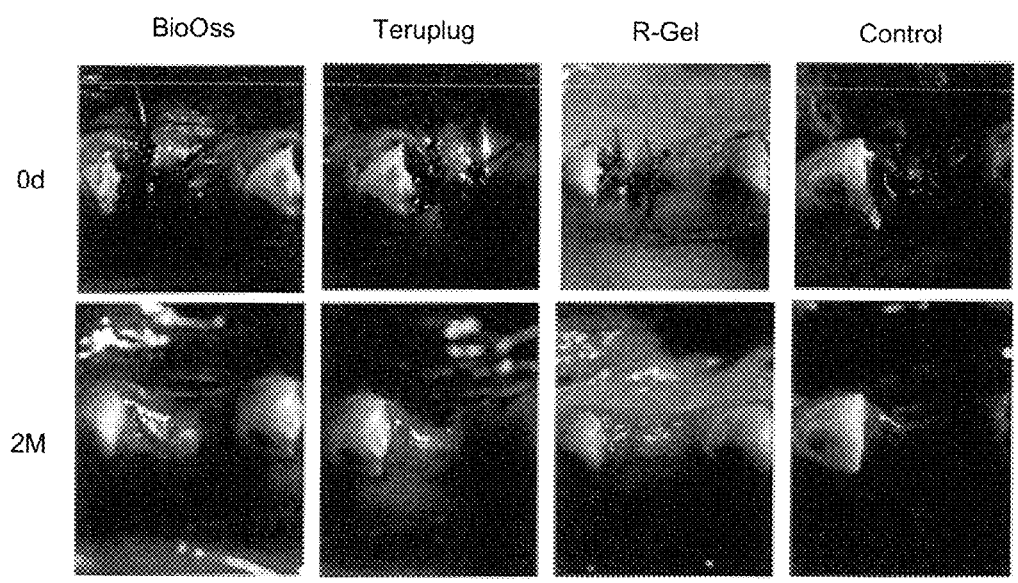
FIG. 11 shows macroscopic photographs of tooth extraction sites of dog mandibular premolar extraction models, which were taken immediately after and two months after transplantation of infills

The thickness of the gingiva in the tooth extraction portion was examined two months after the filling of the tooth extraction portion (FIG. 11). As a result, the thickness of the gingiva was decreased in the case of an untreated control. The thickness of the gingiva was maintained in the portion into which the BioOss Cancellous had been transplanted. The thickness of the gingiva was slightly decreased in the portion into which the Teruplug had been transplanted. In contrast, in the portion into which the R-Gel had been transplanted, the thickness of the gingiva was maintained at the same level as that of the BioOss. That is to say, R-Gel exhibited effectiveness higher than that of Teruplug.

The invention claimed is:

1. A method for inducing bone regeneration which comprises administering a gelatin having the amino acid sequence of SEQ ID NO: 1 or SEQ ID NO: 13, by itself, to a subject at a site in need of bone regeneration.

2. The method of claim 1, wherein the gelatin is crosslinked.

3. The method of claim 2, wherein the crosslinking is carried out using an aldehyde, condensing agent or enzyme.

4. The method of claim 1, wherein the gelatin is in granule form.

5. The method of claim 1, wherein the subject has a bone defect.

6. The method of claim 5, wherein the bone defect is caused by oral surgery, osteoporosis, or arthropathy.

7. A method for supplementing bone which comprises administering a gelatin having the amino acid sequence of SEQ ID NO: 1 or SEQ ID NO: 13, by itself, to a subject at a site in need of bone supplementation.

8. The method of claim 7, wherein the gelatin is in granule form.

* * * * *